United States Patent
Samosky et al.

(10) Patent No.: US 10,325,522 B2
(45) Date of Patent: Jun. 18, 2019

(54) MEDICAL TRAINING SYSTEM AND METHOD OF EMPLOYING

(71) Applicant: UNIVERSITY OF PITTSBURGH—OF THE COMMONWEALTH SYSTEM OF HIGHER EDUCATION, Pittsburgh, PA (US)

(72) Inventors: Joseph T. Samosky, Pittsburgh, PA (US); Douglas A. Nelson, Jr., Meadville, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 40 days.

(21) Appl. No.: 14/372,332

(22) PCT Filed: Jan. 25, 2013

(86) PCT No.: PCT/US2013/023119
§ 371 (c)(1),
(2) Date: Jul. 15, 2014

(87) PCT Pub. No.: WO2013/112815
PCT Pub. Date: Aug. 1, 2013

(65) Prior Publication Data
US 2014/0363801 A1    Dec. 11, 2014

Related U.S. Application Data

(60) Provisional application No. 61/591,494, filed on Jan. 27, 2012.

(51) Int. Cl.
G09B 23/30    (2006.01)
G09B 5/02    (2006.01)
(Continued)

(52) U.S. Cl.
CPC ............... *G09B 23/30* (2013.01); *G09B 5/02* (2013.01); *A61B 5/7435* (2013.01);
(Continued)

(58) Field of Classification Search
CPC ........ G09B 23/285; G09B 23/30; G09B 5/02; G06F 19/3437; A61B 2034/102; A61B 5/7435; A61B 2034/101
(Continued)

(56) References Cited

U.S. PATENT DOCUMENTS 5,853,292 A * 12/1998 Eggert ................ G09B 23/28
434/262
5,959,617 A * 9/1999 Bird ..................... G06F 3/03542
345/182
(Continued)

FOREIGN PATENT DOCUMENTS

| KR | 2011-0065388 | 6/2011 |
| WO | 03-096307 | 11/2003 |
| WO | 2010-034117 | 4/2010 |

*Primary Examiner* — Jack Yip
(74) *Attorney, Agent, or Firm* — Eckert Seamans Cherin & Mellott, LLC; Stephen A. Bucchianeri (57) ABSTRACT

A medical training method includes generating an image of a first level of anatomical structures, displaying the image in a correct registration in a first display area on the surface of a portion of a simulated body, detecting a user input associated with the portion of the simulated body, and responsive to said detecting, generating and displaying at least one visual image in a correct registration in the first display area. A system for carrying out such method is also provided.

26 Claims, 9 Drawing Sheets

(51) Int. Cl.
    *A61B 34/10*     (2016.01)
    *G09B 23/28*     (2006.01)
    *A61B 5/00*     (2006.01)

(52) U.S. Cl.
    CPC ... *A61B 2034/101* (2016.02); *A61B 2034/102* (2016.02); *G09B 23/285* (2013.01)

(58) Field of Classification Search
    USPC .......................................................... 434/267
    See application file for complete search history.

(56) References Cited

U.S. PATENT DOCUMENTS

| | | | | |
|---|---|---|---|---|
| 6,106,463 | A * | 8/2000 | Wilk | A61B 5/742 600/437 |
| 6,428,323 | B1 | 8/2002 | Pugh | |
| 6,544,041 | B1 * | 4/2003 | Damadian | G09B 23/285 434/262 |
| 2004/0234933 | A1 | 11/2004 | Dawson et al. | |
| 2006/0183096 | A1 * | 8/2006 | Riener | G09B 23/30 434/276 |
| 2008/0118115 | A1 * | 5/2008 | Williamson | G06T 15/00 382/128 |
| 2009/0036902 | A1 * | 2/2009 | DiMaio | A61B 8/12 606/130 |
| 2010/0023163 | A1 * | 1/2010 | Kidd | G06N 3/008 700/245 |
| 2010/0167249 | A1 * | 7/2010 | Ryan | G09B 23/285 434/267 |
| 2012/0045742 | A1 * | 2/2012 | Meglan | G09B 23/28 434/268 |
| 2012/0083185 | A1 * | 4/2012 | Bradley | A63H 3/28 446/297 |
| 2012/0315820 | A1 * | 12/2012 | Goff | A63H 3/00 446/297 |
| 2013/0325493 | A1 * | 12/2013 | Wong | G06F 19/00 705/2 |
| 2014/0302931 | A1 * | 10/2014 | Conceicao | A63F 13/20 463/31 |

* cited by examiner

MEDICAL TRAINING SYSTEM AND METHOD OF EMPLOYING

CROSS-REFERENCE TO RELATED APPLICATION

This application claims priority under 35 U.S.C. § 119(e) from U.S. Provisional Application No. 61/591,494, entitled "Bodyexplorer: Enhancing a Mannequin Medical Stimulator with Sensing and Projective Augmented Reality for Exploring Dynamic Anatomy and Physiology", which was filed on Jan. 27, 2012, the disclosure of which is incorporated herein by reference.

FIELD OF THE INVENTION

The present invention relates to medical training tools, and in particular to systems and methods for medical training purposes.

BACKGROUND OF THE INVENTION

Over the past decade medical simulation has been experiencing explosive growth and widespread adoption. There are now over 1000 medical simulation centers in the US alone, in medical schools, nursing schools, hospitals, military simulation centers and schools of allied health professions (e.g., paramedics). Just as flight simulation has enabled risk-free training or pilots and resulted in substantial increases in safety, healthcare training is seeking similar benefits from simulation, including objective, criterion-based training, promotion of patient safety and increases in training efficiency. Simulation offers hands-on, experiential learning without exposing real patients to risk. It enables objective assessment (via sensor-based measurement of performance metrics), standardized practice and the ability to learn from mistakes without harm to a patient.

Although there are many varieties of medical simulators, from simple physical models to haptic-enabled virtual reality systems, the most common simulator is the full-body mannequin trainer. The two largest commercial firms producing such mannequin simulators have over 12,000 systems deployed worldwide. Mannequin simulators are designed to approximate the appearance and some of the clinical responses of a human patient, and offer the ability to display clinical signs such as palpable pulses, blood pressure, chest rise and fall with ventilation, and pupils that dilate in response to light. A fundamental limitation of current mannequins for training is that their internal structures (with limited exceptions such as airways) bear no resemblance to actual human anatomy. Like humans, they are mainly visually opaque. This attribute limits the ability for a student training with the mannequin to perform physical "dissection" on a mannequin or "peer behind the curtain" of the skin surface to explore the internal consequences of their external interventions.

For teaching many patient interactions or procedures (e.g., without limitation, endotracheal tube insertion, Foley catheter placement, bronchoscopy, central line placement) it would be advantageous if patients were "see through" so that a trainee could see what was actually occurring within the body as the trainee manipulated a tool or device. Presently, systems exist that project simulations of internal structures onto a body, however such systems do not allow for interaction by a trainee and do not provide feedback as to foreign structures, such as medical instruments, placed into a body. One such system projects computer generated images of anatomy onto a rigid white body form. The position and orientation of the form is tracked and the images are transformed appropriately so that it appears to users that they can rotate the body and see the internal anatomy from different orientations. Such a system, while offering potential utility for the study of anatomy, does not provide for procedural simulation, i.e., it does not track the position of medical devices and display their internal representations in accurate relationship to internal structures, does not display displacements or other positional alterations of internal structures as they are contacted by medical devices and does not allow interaction with medical devices to be viewed internally. Such system also requires that the images be viewed through a small hand-held window frame which is tracked in order to correct for parallax errors. The use of such viewer window does not lend itself to group learning environments as accurate viewing is limited to a single person at a time.

As such, there exists a need for improved systems and methods for medical teaching and training purposes including, without limitation, those procedures that involve the external manipulation of a medical device that is moving or acting inside the body. There may be significant advantages to a system that during training enables the visualization of the internal portions of tools and devices and the relevant anatomy with which the tools interact. Such real-time, interactive visualizations may permit trainees to develop better mental models of the internal consequences of their external actions. These mental models may in turn help trainees to acquire skills more quickly and efficiently, achieve higher levels of proficiency, and help them more effectively to identify and avoid potential errors that could cause harm in an actual patient.

SUMMARY OF THE INVENTION

In one non-limiting embodiment, the invention provides a medical training method comprising: generating an image of a first level anatomical structures; displaying the image in a correct registration in a first display area on the surface of a portion of a simulated body; detecting a user input associated with the portion of the simulated body; and responsive to said detecting, generating and displaying at least one visual image in a correct registration in the first display area.

Generating and displaying at least one visual image in the first display area may comprise: generating a second image of a second level of anatomical structures different from the first level of anatomical structures and displaying the second image in a second display area within the first display area.

Detecting a user input associated with the portion of the simulated body may comprise: detecting a selection of a first point within the first display area and detecting a selection of a second point within the first display area, wherein displaying the second image comprises displaying the second image in a second display area bounded by the first point and the second point.

The method may further comprise detecting a selection associated with the second display area and responsive thereto, modifying a characteristic of the second display area. Modifying a characteristic of the second display area may comprise changing a dimension of the second display area. Modifying a characteristic of the second display area may comprise changing the position of the second display area within the first display area. Detecting a selection associated with the second display area may comprise detecting a selection associated with an anatomic structure displayed in the second display area and modifying a characteristic of the second display area may comprise displaying an identifier of the anatomic structure within the second display area.

The method may further comprise detecting a selection associated with the identifier of the anatomic structure and responsive thereto, displaying a menu of options associated with the anatomic structure.

The method may further comprise detecting a selection associated with one of the options associated with the anatomic structure and generating additional visual or auditory displays conveying static or dynamic information about the selected anatomic structure.

The method may further comprise generating a third image of a third level of anatomical structures and displaying the third image in a third display area within the second display area.

The method may further comprise generating images of real tools or devices which are interacting with the simulated body, the images being responsive in one or more of position, orientation or configuration to a sensed position, orientation and configuration of the real tools or devices.

The method may further comprise generating images of physiological data streams or other real-time dynamic data which are responsive to sensed inputs to the body, such as administration of simulated drugs, ventilation of the lungs, insertion of catheters, application of pressure, etc.

In another non-limiting embodiment, the invention provides a system for displaying simulated images of internal structures on an exterior surface of a simulated body. The system comprises: a processor; a memory in communication with the processor; a sensing system in communication with the processor, the sensing system structured to detect a user input associated with the simulated body; and a display system in communication with the processor, the display system structured to display images within a display area on the exterior surface of the simulated body. The processor is structured to cause the display system to display a first image of a first predetermined layer of anatomic structures in a correct registration within the display area and to display a second image within the display area in response to a user input detected by the sensing system.

The system may further comprise an input device structured to be detected by the sensing system.

The display system may comprise a projector structured to project the images onto the surface of the simulated body.

The display system may comprise a video display system disposed in or on the surface of the simulated body.

BRIEF DESCRIPTION OF THE DRAWINGS

The accompanying drawings illustrate presently preferred embodiments of the invention, and together with the general description given above and the detailed description given below, serve to explain the principles of the invention. As shown throughout the drawings, like reference numerals designate like or corresponding parts.

DESCRIPTION OF THE PREFERRED EMBODIMENTS

As employed herein, the statement that two or more parts or components are "coupled" together shall mean that the parts are joined or operate together either directly or through one or more intermediate parts or components.

As employed herein, the statement that two or more parts are in "communication", "communicate", or other similar phrasing, shall mean the parts are capable of at least one of sending or receiving electrical signals via a wired or wireless connection.

As employed herein, the term "number" shall mean one or an integer greater than one (i.e., a plurality).

As employed herein, the terminology "simulated body" shall be used to refer to a simulated (i.e., artificial) representation of the body of a living organism (e.g., without limitation, a human or animal body) or a portion thereof.

As employed herein, the terminology "relevant anatomical structures" shall be used to refer to internal anatomical structures that would be present in a living human or animal body at or near a particular location identified in a corresponding simulated body.

As employed herein, the terminology "level of anatomic structures" shall mean a set of anatomic structures that have been preselected and grouped together.

The present invention provides improved systems and methods for medical training purposes. More particularly, embodiments of the present invention enable a simulated body, e.g., without limitation, a human mannequin, to serve as an input surface as well as a display surface for use in medical training operations. Interactions with the surface of the mannequin enable a student or instructor to selectively define and open anatomic windows (or viewports) onto the underlying anatomy. Multiple overlapping viewports can provide the illusion of revealing structures at multiple depths. In one example embodiment, a custom-designed infrared (IR) pen and a set of graphical interactions also enables selection of one or more organs for identification and calling up contextual menus offering the ability to display associated datastreams, such as audio or graphs or physiological parameters related to the selected organ(s).

Images of the underlying anatomy are displayed in real time on the simulated body being interacted with by the student and/or instructor. The images are provided in a manner that allows the student, as well as others, to clearly view the images as if they possessed the power to selectively see into and or through objects (i.e., x-ray vision) throughout the procedure. This enables students to better understand the internal consequences of their external manipulations and aids in the building realistic multi-dimensional mental models of the internal anatomical structures within the body. The ability to provide feedback on performance in real-time (that is, perceptually indistinguishable from instantaneous or nearly so) also offers potential advantages to conventional medical training. For example, when performing endotracheal intubation a common error is to insert the endotracheal tube into the esophagus rather than the trachea. This error may not be detected by the student until some time interval passes, typically until ventilation is attempted and what is seen in response is stomach inflation rather than chest rise and fall. The present invention provides the means to immediately detect and visualize errors such as esophageal intubation, providing proximate, rather than delayed, feedback to the trainee. Providing such feedback proximate to the error may enhance the trainee's understanding of the root cause of the error and corrective actions that should be taken.

A variety of sensor systems may be implemented with the systems and methods described herein that enable a user to interact with the body via naturalistic inputs. For example, systems which recognize drug simulants injected into the simulated body or systems which sense the insertion of a breathing tube (endotracheal tube) and of catheters may be readily incorporated into embodiments of the present invention. These sensed inputs may be used to drive changes in displayed anatomy and physiology.

Figure 1:
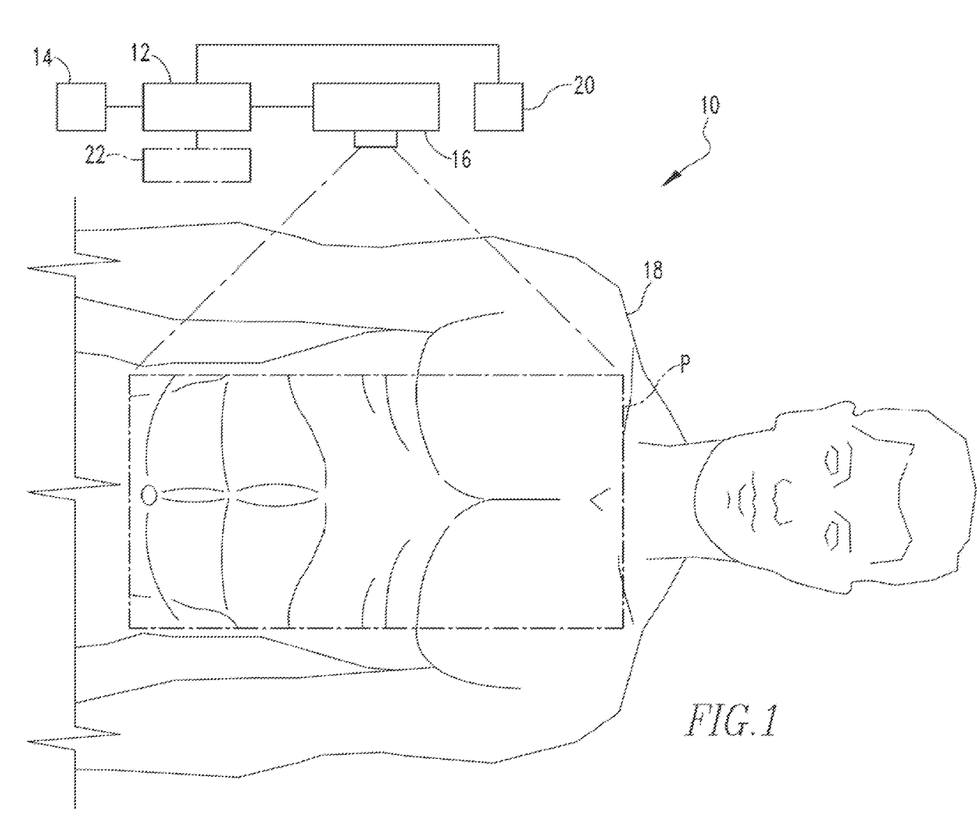
FIG. 1 is a partially schematic view of a training system in accordance with an example embodiment of the present invention.

FIG. 1 shows a partially schematic view of a training system 10 in accordance with an example embodiment of the present invention. Training system 10 includes a processor 12 which may comprise a microprocessor, a microcontroller or some other suitable processing device, that is operatively coupled to a memory 14. The memory 14 can be any of a variety of types of internal and/or external storage media, such as, without limitation, RAM, ROM, EPROM(s), EEPROM(s), and the like, that provide a storage medium for data and software executable by the processor 12 for controlling the operation of other components connected thereto.

Continuing to refer to FIG. 1, training system 10 further includes a display system 16 in communication with the processor 12 such that signals received from processor 12 are transformed into visual images displayed in a correct registration within a display area P on the surface of a simulated body 18. Such images may be generated using computer graphics methods from data models of internal anatomy stored in memory 14 or from prerecorded images of living, or previously living anatomy. Such images may be displayed in a number of ways. As will be discussed in further detail in the example provided herein, a projector system may be employed that projects the images onto a surface of the simulated body 18. Such images could also be displayed using flat or curved displays integrated on or in a surface of the simulated body 18.

In the example embodiment shown in FIG. 1, display system 16 is disposed generally above the simulated body 18 and the display area P comprises a detailed image of the skin surface of the torso region of a male human body disposed in a correct registration on the simulated body 18. Such simulated body 18 includes a number of anatomical features designed to closely imitate actual biologic features. Although shown generally as the upper portion of a human mannequin, it is to be appreciated that simulated body 18 may be in the form of other organisms or relevant portions thereof. The display system 16 is in electronic communication with, and receives display signals from, the processor 12.

In an example embodiment of the present invention, processor 12 and memory 14 are embodied by either of a desktop or laptop computer disposed in relative proximity to the simulated body 18. It is to be appreciated, however, that other processors and memory may be employed without varying from the scope of the present invention and that such other processors and memory may be disposed external or internal to the simulated body without varying from the scope of the present invention.

Figure 2:
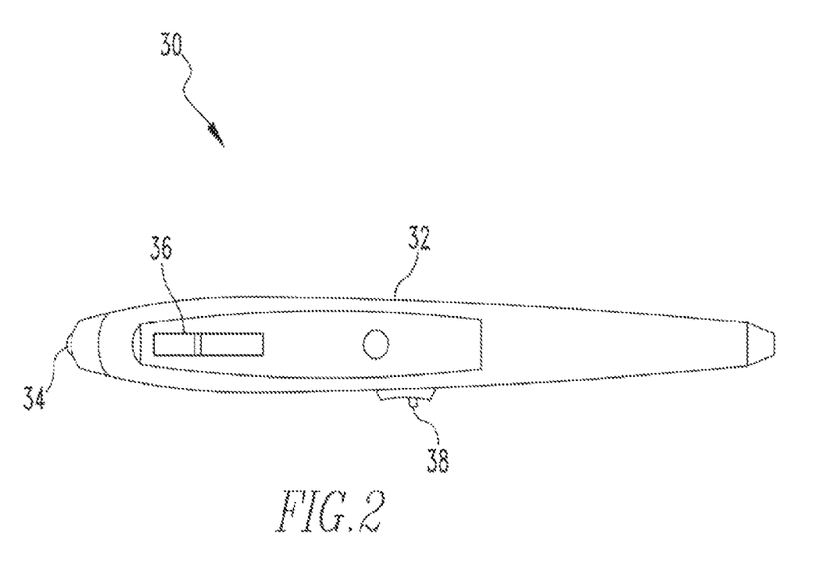
FIG. 2 is a side view of an example input device in accordance with an embodiment of the present invention.

In order to provide for interactivity by students and/or instructors during training sessions, training system 10 includes a sensing system 20 in electrical communication with the processor 12. Sensing system 20 is adapted to selectively detect inputs made by one or more of the students and/or instructors taking part in the training system. In the example embodiment illustrated, an input device 30 such as illustrated in FIG. 2, discussed in detail below, is employed to provide input to the system 10. It is to be appreciated, however, that sensing system may be structured to detect input from other devices or simply from a human hand (e.g., without limitation via sensed Motion or through touch sensitive means). Data may be transmitted from the sensing system 20 (described in greater detail below) to the processor 12 so that such data may be manipulated, logged or otherwise utilized as described elsewhere herein. As an alternative, or in addition to, the inputs received by the sensing system 20, other input devices 22 (shown in phantom line in FIG. 1) may be in electrical communication (either wired or wirelessly) with processor 12. Such input devices might include, for example, without limitation, accelerometers, gyroscopes or inertial measurement units (IMU) to detect positioning or changes thereto of a body or device manipulated external or internal to the simulated body 18.

FIG. 2 is a side view of an example input device 30 that is employed in the training system 10 as a mechanism for allowing one or more of the students and/or instructors to interact with the system 10 during a training session, as will be discussed in greater detail in the example scenarios below. Input device 30 generally includes an elongate pen-shaped housing 32 having an IR light emitting diode (LED) 34 disposed in an end (not numbered) thereof, a wireless mouse button 36 disposed in a side portion (not numbered) thereof, and a switch mechanism 38 disposed in a side portion (not numbered) thereof, for selectively switching the LED 34 between on and off positions. Although not particularly shown in FIG. 2, it is to be appreciated that necessary wiring and power supply for the LED 34, mouse button 36, and switch mechanism 38 are provided within housing 32 along with the necessary hardware to provide for wireless connectivity of the mouse button functionality with processor 12.

In operation, the LED 34 of input device 30 functions to provide for the location of input device 30 relative to the simulated body 18, and more particularly the end portion of device 30 at LED 34, to be determined by sensing system 20 in the example embodiment shown, a commercially available Nintendo Wii remote (Wiimote) is employed as sensing system 20 in conjunction with a modified version of the open-source software Wiimote Whiteboard (Johnny Chung Lee, http://johnnylee.net/projects/wii). In such embodiment, the wireless mouse button 36 is then employed for providing indications at particular locations. Such indications may be made by clicking or releasing the mouse button depending on the particular arrangement.

Having thus described the basic components of the example training system 10 and the functioning thereof, a number of example functional embodiments of the system 10 will now be described in conjunction with FIGS. 3-10. As the differences in the embodiments occur only with the images displayed on the simulated body 18, only the simulated body 18 and the displayed images are shown in such FIGS.

In general, interactions with the system 10 may be generally divided into two basic interaction modes in which students or instructors may interact with the system 10, a viewport mode and an explore mode. As discussed in greater detail below, the viewport mode allows for a user to create, resize and move viewports. As will be discussed in greater detail below, such viewports provide for the selective viewing of internal structures in the body in a manner as if the intervening structures were removed or made invisible. In the explore mode, a user is able to interact with internal structures and selectively view multimedia data related to such structures.

Figure 3:
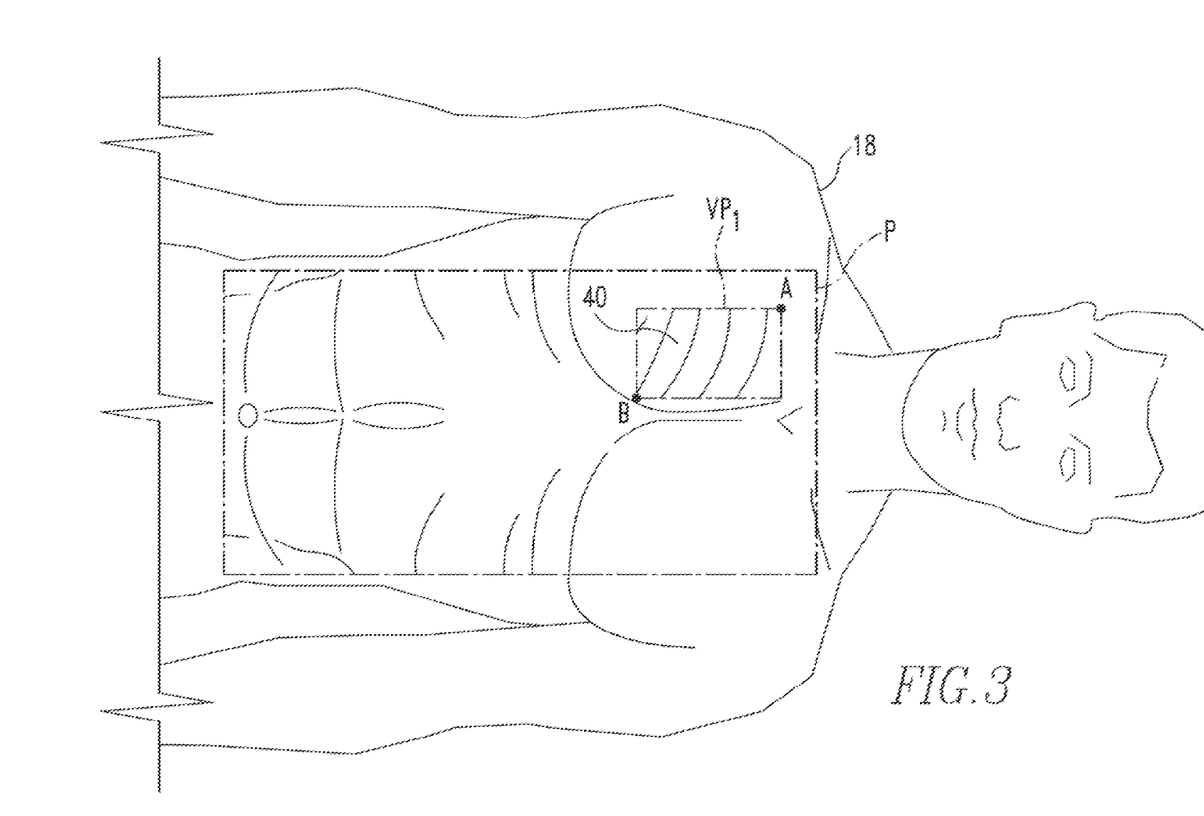
FIGS. 3-10 are schematic representations of embodiments of the present invention displayed on a portion of the training system of FIG. 1.

FIG. 3 shows an example embodiment of a system in accordance with an embodiment of the present invention operating in viewport mode. More particularly, FIG. 3 shows a second display area, viewport $VP_1$, created within the display area P. Similar to the image displayed in the display area P in FIG. 1, which showed an image of the skin surface, the majority of the display area P still contains such image. However, in the display area delimited by the first viewport $VP_1$, the outer layers of skin have been removed and a predetermined level of anatomic structures, in this instance the underlying muscle tissue, is displayed in a second image in a correct registration on the simulated body 18. Hence the viewport $VP_1$ acts as a viewing portal (i.e., viewport) into the body.

Such viewport $VP_1$ may be created in a number of ways without varying from the scope of the present invention. However, in the example shown in FIG. 3, the viewport $VP_1$ was created by first placing the IR LED 34 of input device 30 on or near the surface of the simulated body 18 at point "A" and then clicking the mouse button 36, thus providing an indication of the location of a boundary of the viewport $VP_1$. Next the input device 30 was moved such that the IR LED 34 was on or near the surface of the simulated body at point "B", and once there the mouse button 36 was once again clicked, thus providing another indication of the location of a boundary of the viewport $VP_1$. It is to be appreciated that such example input scenario is given for example purposes only and that other combinations of inputs may be employed for creating one or more viewports without varying front the scope of the present invention.

Figure 4:
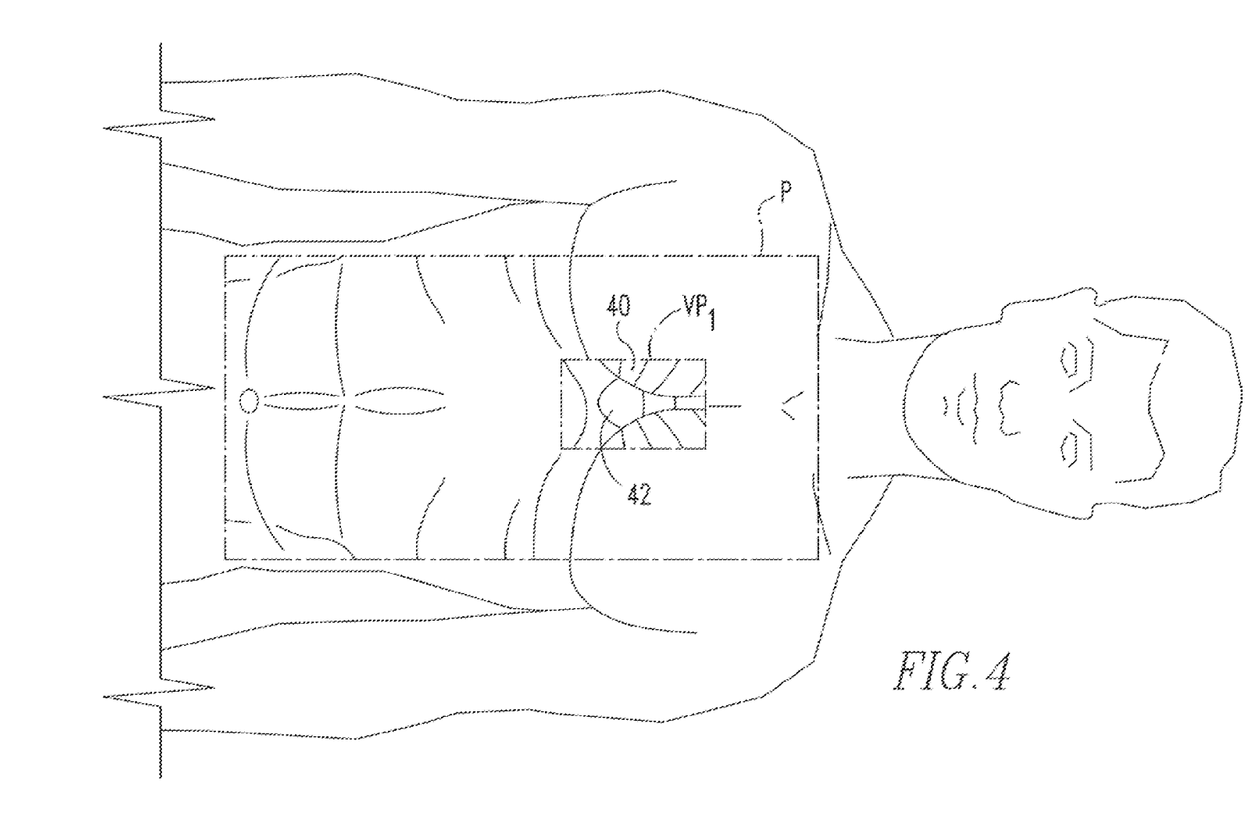

Once a viewport, e.g., without limitation, viewport $VP_1$, has been created, one or more characteristics of the viewport $VP_1$ may be selectively modified. For example, FIG. 4 shows a further embodiment of the present invention in which the viewport $VP_1$ has been moved from its original location generally over the right pectoral muscle, as shown in FIG. 3, to a location generally about the sternum 42 of the simulated body. Such movement may be accomplished in a number of ways. In the present embodiment, such movement was accomplished by placing the IR LED 34 of input device 30 on a point within the viewport $VP_1$ and then clicking and holding the mouse button 36, thus providing an indication to begin the moving process. Next, while still holding the mouse button 36, the viewport $VP_1$ as then dragged to its new location about the sternum 42 of the patient, where at the mouse button 36 was subsequently released, thus providing an indication to end the moving process.

Figure 5:
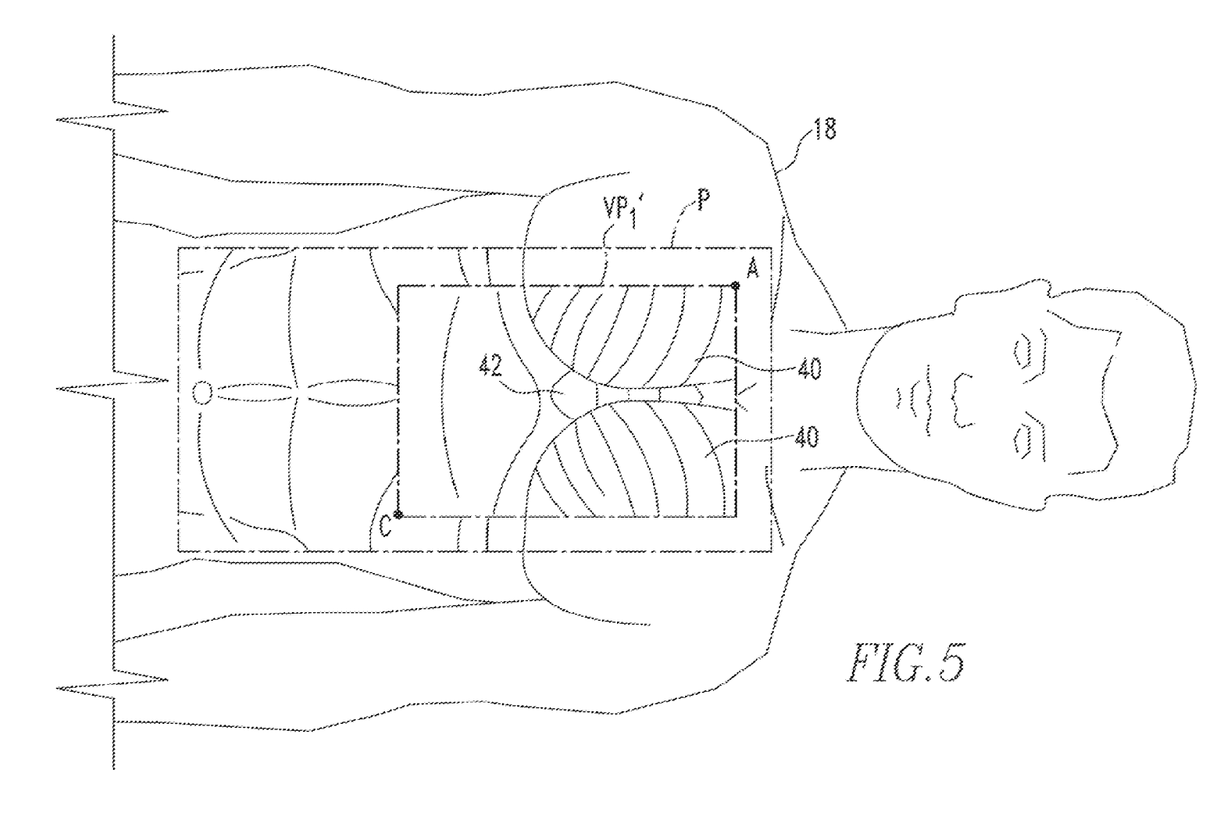

Another characteristic of a viewport that may be selectively modified is the size of the viewport. For example, FIG. 5 shows an embodiment in which the viewport $VP_1$ of FIG. 3 has been enlarged, thus forming the larger viewport $VP_1'$. In such example, such enlargement was carried out by first placing the IR LED 34 of input device 30 on or near the surface of the simulated body 18 at or near the corner, point "B", of the viewport $VP_1$ of FIG. 3 and then pressing and holding the mouse button 36 (thus providing an indication that the corner was going to be dragged to enlarge the associated viewport). Next the IR LED 34 was moved to point C of FIG. 5 where at the mouse button 36 was subsequently released (thus providing an indication that the dragging was done and the corner cold be released).

Figure 6:
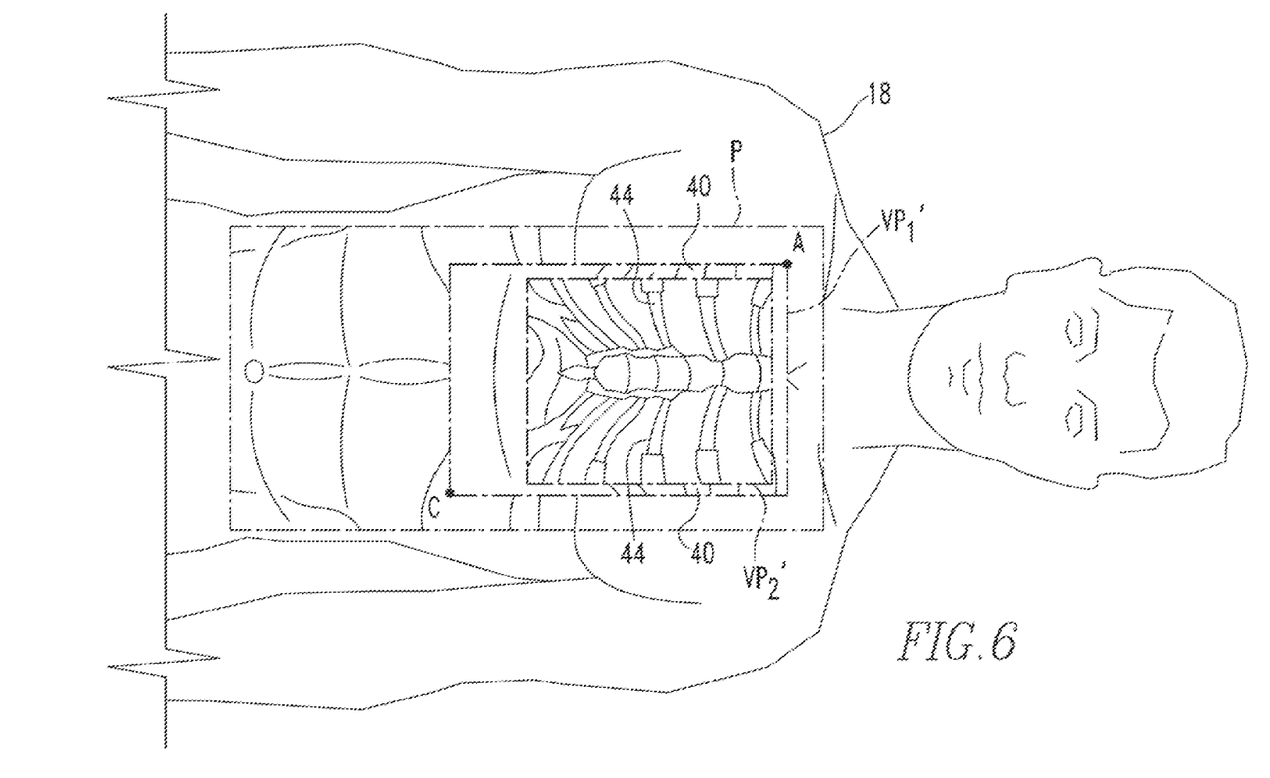

FIG. 6 shows yet another example feature of the present invention in which a second viewport $VP_2'$, showing a yet deeper anatomic layer (e.g., ribs 44 in a correct registration on the simulated body 18, has been created within the larger viewport $VP_1'$, previously described in conjunction with FIG. 5 (and thus also within the display area P). Such second viewport $VP_2'$ was created in a similar manner as the viewport $VP_1$ previously described in conjunction with FIG. 3. It is to be appreciated that FIG. 6 thus shows three different anatomic layers within the display area P.

Figure 7:
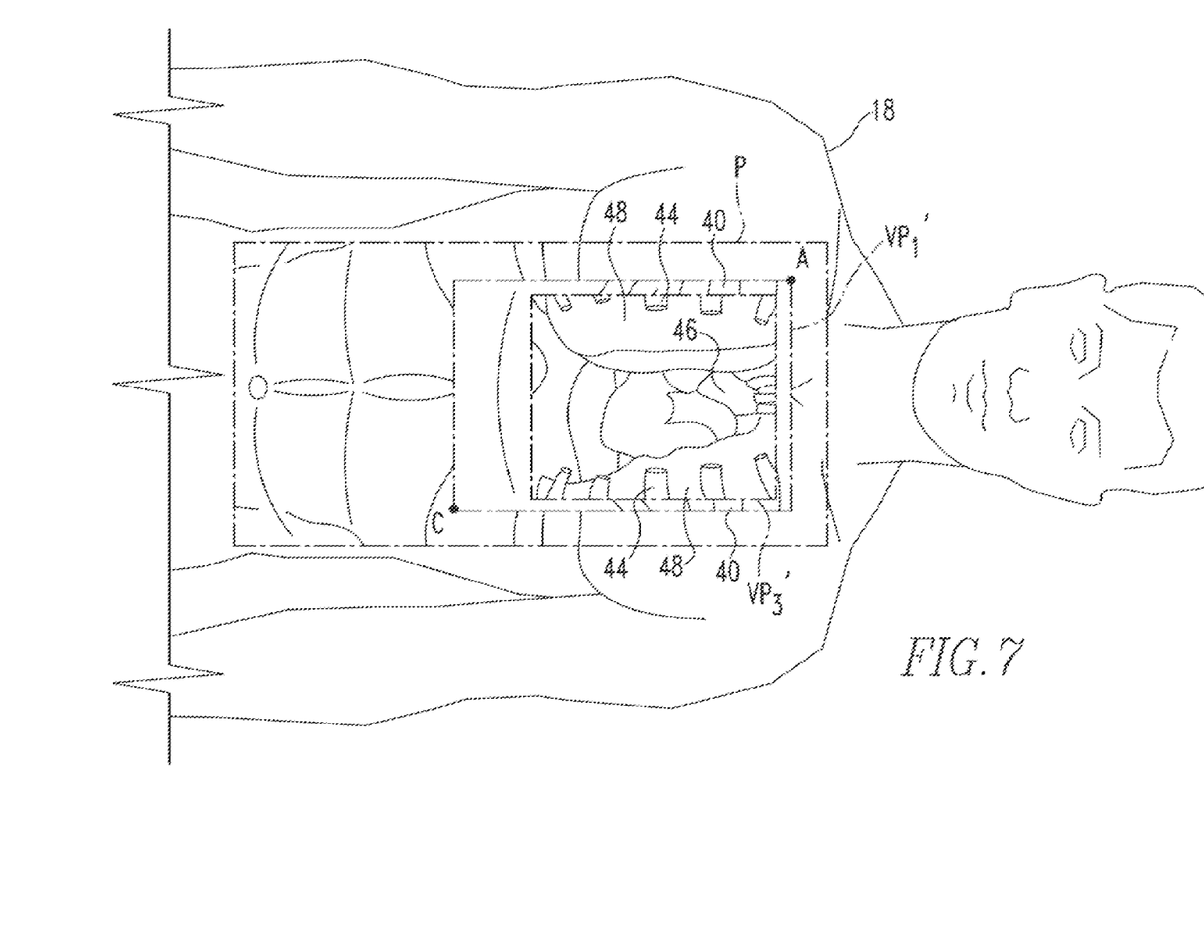

FIG. 7 shows another example embodiment of the present invention in which a viewport has been created within another viewport as previously discussed in conjunction with FIG. 6. Unlike the embodiment discussed in conjunction with FIG. 6 in which the "inner" viewport $VP_2'$ revealed an anatomic layer basically one lower than that displayed in $VP_1'$, the "inner" viewport $VP_3'$ of FIG. 7 displays an anatomic layer basically two lower, i.e., below ribs 44, revealing the heart 46, lungs 48 and other related anatomic structures positioned in a correct registration on the simulated body 18.

Figure 8:
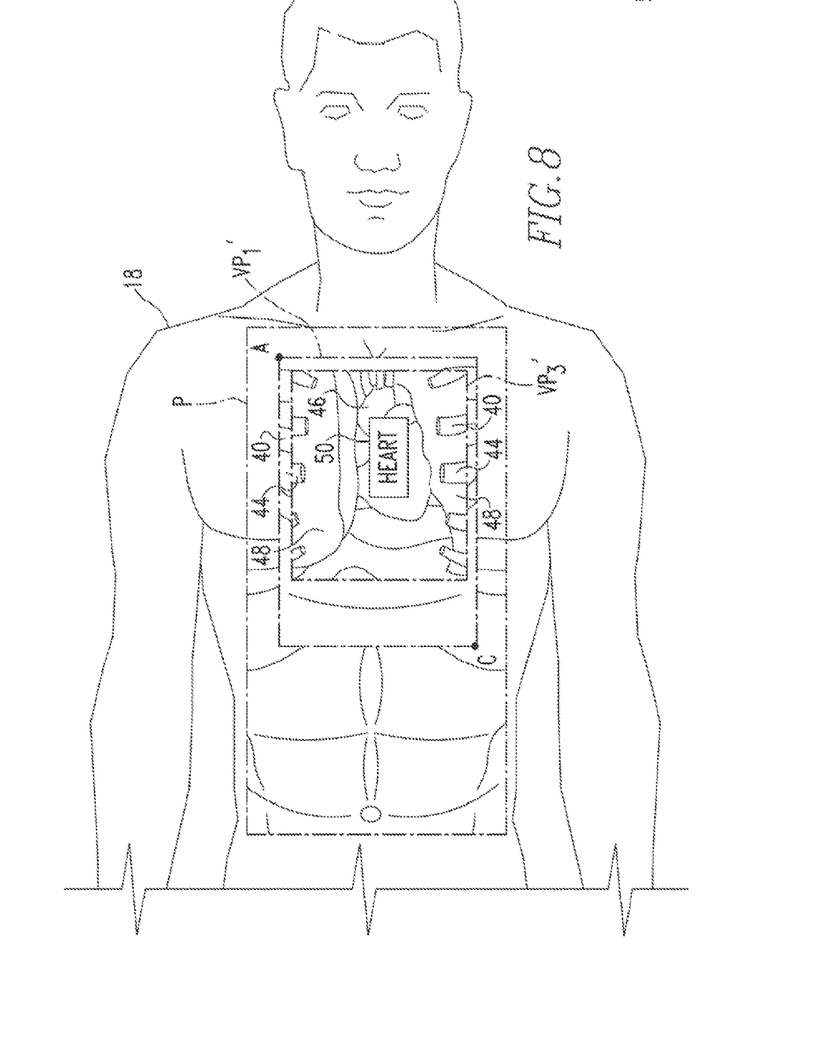
Figure 9:
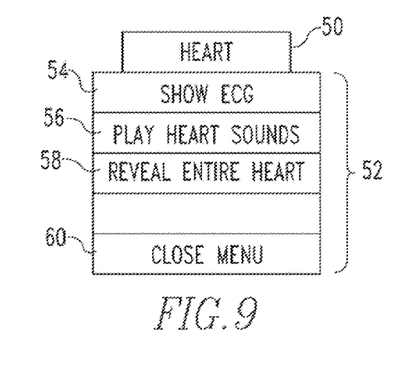
Figure 10:
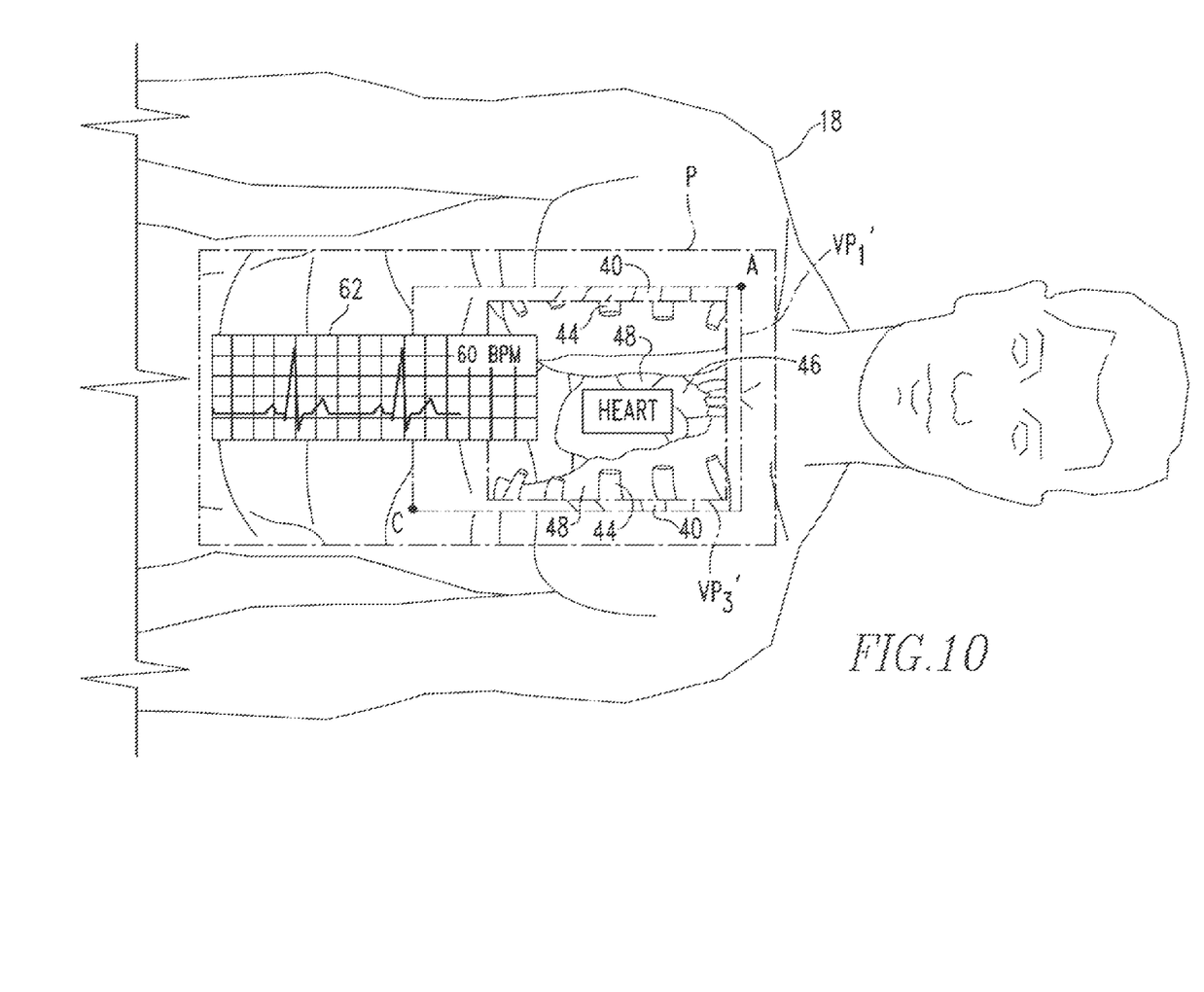

FIG. 8 shows yet another example embodiment of the present invention in which demonstrates an anatomic structure identification feature. In the embodiment, the IR LED 34 of input device 30 was positioned on a portion of the heart 46 and the identifier 50 providing the label "HEART" was then displayed on the selected anatomic structure (heart 46). Such feature could similarly be used to identify other anatomic structures contained in the open viewports present within the display area P. If the identifier 50 is subsequently selected by hovering the IR LED 34 thereon and depressing mouse button 36, a drop down contextual menu 52 having a number of further selectable options 54, 56, 58 and 60 is displayed extending from the identifier 50 within display area P. An example embodiment of such an identifier 50 and associated drop down contextual menu 52 is shown in FIG. 9. Further selection of one of the options (e.g., without limitation, options 54, 56, 38 and 60) causes the processor 12 to carry out the selected visual or audio option. FIG. 10 provides an example embodiment in which option 54, "show ECG" of FIG. 9 was selected, thus causing a sample ECG to be displayed in a new window 62 displayed within the display area P. Window 62 may be moved, as needed, through conventional drag and drop functions.

Other context-dependent options, that is, options which are specific to a particular organ or structure, may be selected to display additional information associated with particular organs or structures, including, without limitation, sounds such as heart sounds or lung sounds, or physiological data streams providing information on organ or physiological system parameters or performance.

While preferred embodiments of the invention have been described and illustrated above, it should be understood that these are exemplary of the invention and are not to be considered as limiting. Additions, deletions, substitutions, and other modifications can be made without departing from the spirit or scope of the present invention. Accordingly, the invention is not to be considered as limited by the foregoing description but is only limited by the scope of the appended claims.

What is claimed is:
1. A medical training method comprising:
generating an image of a first set of anatomical structures;
displaying the image onto a surface of a physical anatomic model, the image being in correct registration with surface landmarks on the physical anatomic model, and the image being located in a first display area on the surface of the physical anatomic model;

detecting a first interaction by the user with a location on the surface of the physical anatomic model that is within the first display area, said interaction indicating the location of a first point within the first display area, detecting a second interaction by the user with another location on the surface of the physical anatomic model that is within the first display area, said interaction indicating the location of a second point within the first display area; and responsive to detecting the second interaction, generating and displaying a new visual image in a correct registration in the first display area on the surface of the physical anatomic model, wherein generating and displaying the new visual image in the first display area on the surface of the physical anatomic model comprises:

generating a second image of a second set of anatomical structures different from the first set of anatomical structures; and displaying the second image in a second display area defined by and bounded by the first point and the second point within the first display area, and wherein the second image comprises a view of an underlying or subjacent anatomical structure or structures, the view providing the visual appearance of a viewport providing a visualization of the underlying or subjacent anatomical structure or structures which coincide with the second display area.

2. The method of claim 1 further comprising detecting an interaction by the user with the surface of the physical anatomic model associated with the second display area, and responsive thereto, modifying a characteristic of the second image displayed in the second display area.

3. The method of claim 2 wherein modifying a characteristic of the second image displayed in the second display area comprises changing a dimension or aspect ratio of a boundary of the viewport displayed in the second display area.

4. The method of claim 2 wherein modifying a characteristic of the second image displayed in the second display area comprises changing the position of the viewport displayed in the second display area within the boundaries of the first display area.

5. The method of claim 2 wherein detecting an interaction by the user with the surface of the physical anatomic model associated with the second display area comprises detecting a selection associated with an anatomic structure displayed in the second display area; and wherein modifying a characteristic of the second image displayed in the second display area comprises displaying an identifier of the anatomic structure within the second display area.

6. The method of claim 5 further comprising detecting a selection associated with the identifier of the anatomic structure and responsive thereto, displaying a menu of options associated with the anatomic structure.

7. The method of claim 6 further comprising detecting a selection associated with one of the options associated with the anatomic structure and generating additional visual or auditory displays conveying static or dynamic information about the selected anatomic structure.

8. The method of claim 1 wherein the viewport comprises a first viewport and wherein the method further comprises: generating a third image of a third set of anatomical structures and displaying the third image in a third display area within the second display area, the third display area providing the visual appearance of a second viewport within the first viewport.

9. The method of claim 8 wherein the boundary of the third display area is continuously updated in real time to provide a perceptually smooth modification of the size and dimensions of the second viewport providing visualization of the underlying or subjacent anatomical structures within the third display area.

10. The method of claim 1 further comprising: generating images of real tools or devices which are interacting with the physical anatomic model, said images being responsive in one or more of position, orientation or configuration to a sensed position, orientation and configuration of the real tools or devices.

11. The method of claim 1 further comprising:
generating images of and displaying onto the physical anatomic model physiological data streams.

12. The method of claim 11 wherein the physiological data streams or other real-time dynamic data displayed onto the physical anatomic model are responsive to sensed user interactions with the physical anatomic model.

13. The method of claim 11, wherein the physiological data streams comprise an electrocardiograph waveform or other real-time dynamic data.

14. The method of claim 1 wherein detecting the first interaction and detecting the second interaction each comprise detecting an input received from an input device which is grasped by the user, is separate from the physical anatomic model, and is employed by the user directly on the surface of the physical anatomic model to indicate locations on the surface of the physical anatomic model.

15. The method of claim 1 wherein the image of a first set of anatomical structures comprises a simulation of the visual appearance of the skin surface of the region of a real body corresponding to the portion of the physical anatomic model.

16. The method of claim 1 wherein the second display area is rectangular in shape and wherein the first point and the second point define the opposite corners of the second display area.

17. The method of claim 1 wherein the second interaction occurs over a period of time and indicates a plurality of second points, and wherein the boundary of the second display area is continuously updated in real time to provide a perceptually smooth modification of the size and dimensions of the viewport providing visualization of the underlying or subjacent anatomical structures within the second display area.

18. The method of claim 1 wherein the physical anatomic model constitutes a full-body mannequin medical simulator.

19. The method of claim 1 wherein the physical anatomic model constitutes a partial-body mannequin medical simulator.

20. The method of claim 1 wherein the physical anatomic model is a human being.

21. A system for displaying simulated images of internal structures onto an exterior surface of a physical anatomic model, the system comprising:
a processor;
a memory in communication with the processor;
a display system in communication with the processor, the display system structured to display images within a first display area on the exterior surface of the physical anatomic model; and
a sensing system in communication with the processor, the sensing system structured to:

detect a first interaction by a user with a location on the surface of the physical anatomic model that is within the first display area, said interaction indicating the location of a first point within the first display area, detect a second interaction by the user with another location on the surface of the physical anatomic model that is within the first display area, said interaction indicating the location of a second point within the first display area;

wherein the processor is structured to generate images of predetermined anatomic structures and cause the display system to display a first image of a first predetermined set of anatomic structures in a correct registration within the first display area on the surface of the physical anatomic model, said display being in a correct registration with surface landmarks on the physical anatomic model, and to display a second image of a second set of anatomic structures in a second display area within the first display area which is bounded by the first point and the second point detected in the first interaction and the second interaction of the user with locations on the surface of the physical anatomic model.

22. The system of claim 21 further comprising an input device structured to be detected by the sensing system and employed by the user to interact with the surface of the physical anatomic model to indicate the location of a point on the surface of the physical anatomic model.

23. The system of claim 22 wherein the input device comprises:

an elongate housing sized and structured to be grasped by a user;

an infrared light emitting diode disposed at or about an end of the housing; and an input mechanism disposed on the housing, the input mechanism structured to be selectively actuated by the user.

24. The system of claim 21 wherein the display system comprises a projector structured to project the images onto the surface of the physical anatomic model.

25. The system of claim 21 wherein the display system comprises a video display system disposed in or on the surface of the physical anatomic model.

26. A medical training method which utilizes a system comprising a physical anatomic model, and an input device grasped by the user and separate from the physical anatomic model, the method comprising:

detecting an interaction by the user consisting of grasping the input device by hand and moving it to a location on the surface of the physical anatomic model; said interaction indicating the location of a first point on the surface of the model;

detecting a second interaction by the user with the input device and the surface of the physical anatomic model indicating the location of a second point on the surface of the model, different from the first point;

responsive to the user's indications of the first and second points on the surface of the physical anatomic model, generating at least one visual image of a first subset of subjacent anatomic structures; and displaying the at least one visual image of the first subset of subjacent anatomic structures in correct registration in a first display area on the surface of the physical anatomic model, the boundary, size and location of the first display area being determined by the detected inputs of the location of the first point and the location of the second point on the surface of the physical anatomic model.

* * * * *

UNITED STATES PATENT AND TRADEMARK OFFICE
CERTIFICATE OF CORRECTION

PATENT NO. : 10,325,522 B2
APPLICATION NO. : 14/372332
DATED : June 18, 2019
INVENTOR(S) : Joseph T. Samosky et al.

Page 1 of 1

It is certified that error appears in the above-identified patent and that said Letters Patent is hereby corrected as shown below:

In the Specification

Column 2, Line 39, "structures" should read --structure--.
Column 6, Line 6, "Motion" should read --motion--.
Column 7, Line 49, "where at" should read --whereat--.
Column 7, Line 63, "where at" should read --whereat--.
Column 7, Line 65, "cold" should read --could--.

Signed and Sealed this
Twentieth Day of August, 2019

Andrei Iancu
*Director of the United States Patent and Trademark Office*